United States Patent
Srinivasan et al.

(10) Patent No.: US 8,425,422 B2
(45) Date of Patent: Apr. 23, 2013

(54) ADAPTIVE VOLUME RENDERING FOR ULTRASOUND COLOR FLOW DIAGNOSTIC IMAGING

(75) Inventors: Seshadri Srinivasan, Santa Clara, CA (US); Patric Ljung, Princeton, NJ (US); Bruce A. McDermott, Bellevue, WA (US); Merv Mencias Smith-Casem, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 818 days.

(21) Appl. No.: 12/433,649

(22) Filed: Apr. 30, 2009

(65) Prior Publication Data

US 2009/0306503 A1    Dec. 10, 2009

Related U.S. Application Data

(60) Provisional application No. 61/059,688, filed on Jun. 6, 2008.

(51) Int. Cl.
*A61B 5/00* (2006.01)
(52) U.S. Cl.
USPC .......... 600/443; 600/437; 600/440; 600/441; 600/453; 600/454; 600/407; 382/128; 382/134
(58) Field of Classification Search .................. 600/437, 600/440, 441, 443, 453, 454; 382/128, 134
See application file for complete search history.

(56) References Cited

U.S. PATENT DOCUMENTS

| | | | | |
|---|---|---|---|---|
| 5,720,291 A | * | 2/1998 | Schwartz | 600/456 |
| 5,957,138 A | * | 9/1999 | Lin et al. | 600/453 |
| 6,116,244 A | | 9/2000 | Hossack et al. | |
| 6,280,387 B1 | * | 8/2001 | Deforge et al. | 600/454 |
| 6,500,125 B1 | * | 12/2002 | Muzilla et al. | 600/454 |
| 6,503,202 B1 | | 1/2003 | Hossack et al. | |
| 2004/0081340 A1 | * | 4/2004 | Hashimoto | 382/128 |
| 2005/0113689 A1 | | 5/2005 | Gritzky | |
| 2005/0113960 A1 | * | 5/2005 | Karau et al. | 600/425 |
| 2005/0165308 A1 | | 7/2005 | Jacob et al. | |
| 2006/0098853 A1 | | 5/2006 | Roundhill et al. | |
| 2006/0173326 A1 | | 8/2006 | Thiele | |
| 2007/0167771 A1 | | 7/2007 | Olstad | |
| 2007/0255138 A1 | | 11/2007 | Kristofferson et al. | |

OTHER PUBLICATIONS

Petersch et al. "Blood Flow in Its Context: Combining 3D B-Mode and Color Doppler Ultrasonic Data," Visualization and Computer Graphics, IEEE Transactions on , vol. 13, No. 4, pp. 748-757, Jul.-Aug. 2007. doi: 10.1109/TVCG.2007.1018.*

* cited by examiner

*Primary Examiner* — Unsu Jung
*Assistant Examiner* — Phong K Huynh

(57) ABSTRACT

Adaptive volume rendering is provided for medical diagnostic ultrasound. The opacity of B-mode data is set relative to the opacity of Doppler data. The opacities for the different types of data are set as a function of ray depth. For example, the opacity of B-mode data near a tissue border is set to be more opaque than for tissue away from the border, and the opacity for flow data near a flow border is set to be less opaque than for flow away from the border. An image is rendered using a rendering parameter set as a function of ray depth, B-mode information and Doppler information. Other processes for enhancing and/or using rendering may be used.

17 Claims, 3 Drawing Sheets

ADAPTIVE VOLUME RENDERING FOR ULTRASOUND COLOR FLOW DIAGNOSTIC IMAGING

CROSS-REFERENCE TO RELATED APPLICATIONS

The present patent document claims the benefit of the filing date under 35 U.S.C. §119(e) of Provisional U.S. Patent Application Ser. No. 61/059,688, filed Jun. 6, 2008, which is hereby incorporated by reference.

BACKGROUND

This present invention relates to medical diagnostic ultrasound. In particular, volume rendering is provided for ultrasound color flow diagnostic imaging.

To image flow in a patient, the user positions the transducer at a desired location. Due to the sensitivity of the flow to the angle of insonification, the transducer is repositioned to identify the location with the best image. However, this repositioning may result in longer examination.

Flow imaging includes other variables. The user adjusts the overall gain and image depth gains and velocity scale settings. Proper settings may improve the flow sensitivity and fill-in. However, even images acquired with proper settings may have flow holes or insufficient sensitivity.

Flow imaging may include three-dimensional rendering. A volume is scanned, and flow data is estimated for the volume. The rendering may also incorporate B-mode data. However, the B-mode data and flow data may interfere with each other, reducing the usefulness of the rendered image.

BRIEF SUMMARY

By way of introduction, the preferred embodiments described below include a method, system, computer readable medium, and instructions for adaptive volume rendering in medical diagnostic ultrasound. An image is rendered using a rendering parameter set as a function of depth along the viewing direction (ray), B-mode information and Doppler information. For example, the opacity of B-mode data is set relative to the opacity of Doppler data. The opacities for the different types of data are set as a function of ray depth. For example, the opacity of B-mode data near a tissue border is set to be more opaque than for tissue away from the border, and the opacity for flow data near a flow border is set to be less opaque than for flow away from the border. Other processes for enhancing and/or using rendering may be used.

In a first aspect, a method is provided for adaptive volume rendering in medical diagnostic ultrasound. B-mode and flow ultrasound data representing a volume of a patient is acquired. A viewing direction relative to the volume is received. Values for at least one rendering parameter are determined as a function of ray depth, the B-mode ultrasound data, and the flow ultrasound data. An image is rendered from the B-mode and flow ultrasound data. The rendering is a function of the viewing direction and the values for the at least one rendering parameter.

In a second aspect, a computer readable storage medium has stored therein data representing instructions executable by a programmed processor for adaptive volume rendering in medical diagnostic ultrasound. The storage medium includes instructions for receiving B-mode data and flow data representing a volume, locations in the volume corresponding to either B-mode data or flow data, determining B-mode gradients along ray lines, determining flow gradients along the ray lines, setting values for opacity as a function of depth along the ray lines, the values of the opacity for ray depths associated with flow data being more opaque for locations with lesser flow gradient and being less opaque for locations with greater flow gradient, and the opacity for ray depths associated with B-mode data being more opaque for locations with greater B-mode gradients and being less opaque for locations with lesser B-mode gradients, and rendering an image as a function of the values for the opacity, the B-mode data, and the flow data.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF SPECIFIC EMBODIMENTS

Volume image rendering adapts to both B-mode and color parameters. Volume imaging enhancements include surface and boundary enhancements for B-mode and Color flow images, bleed and noise reduction for color flow, and fill-in and sensitivity improvements for color flow. Identification of the anatomy of tissue may be facilitated using the color flow and B-mode information. Subsequent enhancements using the anatomy include texture enhancement of B-mode, speckle reduction, regional contrast enhancement, identification of clinical markers, color fill-in improvements, velocity-angle correction and enhancing jets, and automated calculations. The various features described herein may be used alone or in combination.

The presentation of color and B-mode is enhanced in 3D imaging. Volumetric B-mode and color information are used to enhance the presentation of B-mode and color Doppler in 3D modes. Color Doppler volume rendering is obtained by a) varying at least one of the rendering parameters (e.g., opacity or fade) as a function of ray depth, B-mode and at least one color Doppler parameter. The varying may be done in multiple passes. Color parameters may include velocity or energy. Boundaries represented by the Color data may be enhanced through a) multi-pass thresholding using the spatial variance of velocity, and b) unfiltered energy and B-mode based thresholding during rendering or ray tracing. Improved sensitivity and fill-in of the color flow image and improved presentation of the B-mode and color images provide improved plunkability and reduced scanning time.

Figure 1:
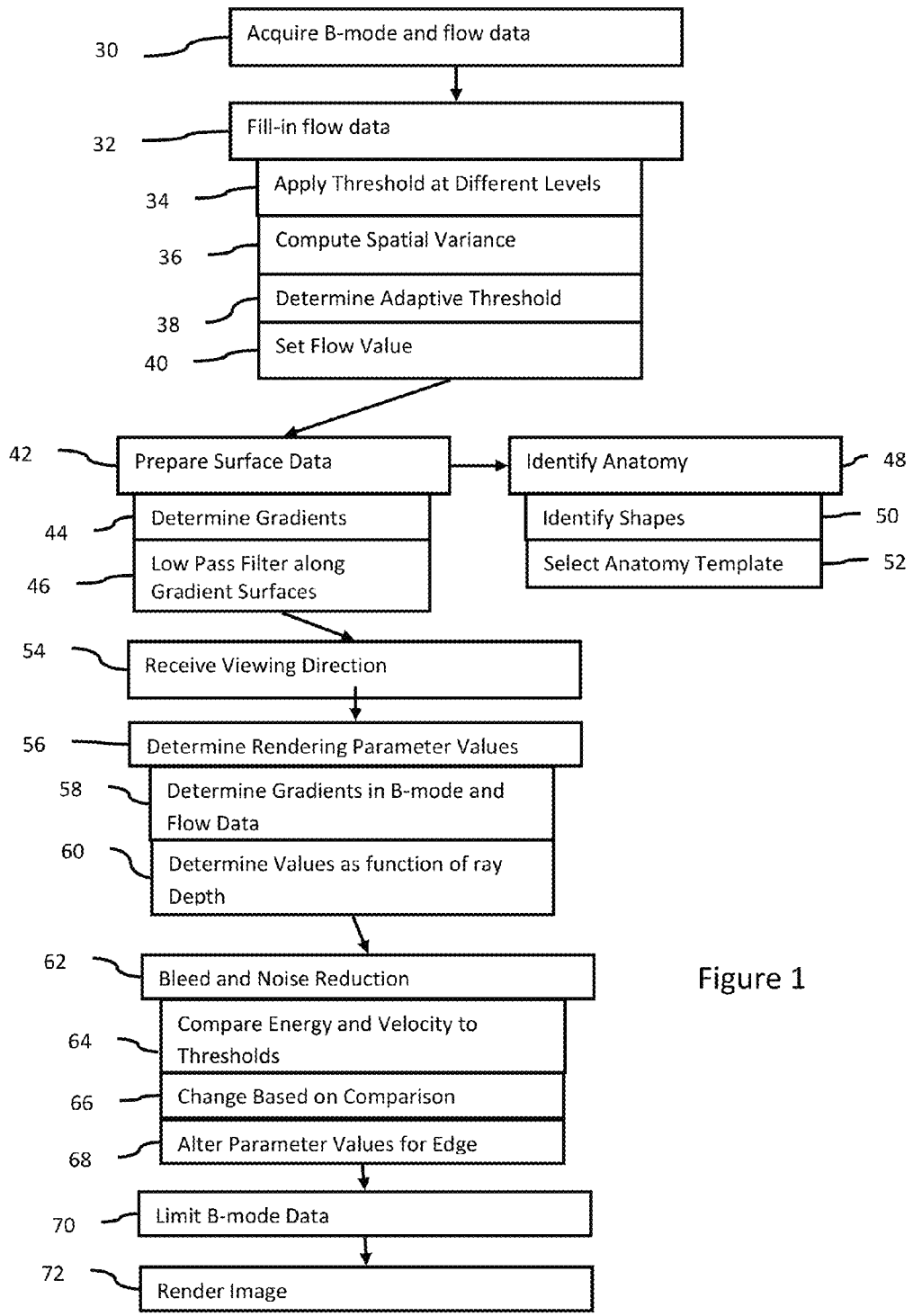
FIG. 1 is a flow chart of one embodiment of a method for adaptive volume rendering.

FIG. 1 shows a method for adaptive volume rendering in medical diagnostic ultrasound. The method is performed by the system 10 of FIG. 4 or a different system. The acts of FIG.

1 are performed in the order shown or a different order, according to specific embodiments. Additional, different or fewer acts than shown in FIG. 1 may be used in some specific embodiments. For example, acts 56-60 are performed without any other acts. As another example, any combination of acts 32, 42, 48, 56, 62, and 70 are provided. Acts 48-52 are for anatomy identification rather than rendering, but may be provided with rendering. The acts of FIG. 1, described below, may be implemented in different ways. At least one example embodiment is provided below, but other embodiments are possible.

In act 30, B-mode and flow ultrasound data are acquired. B-mode data represents intensities. Flow data are estimates of velocity, energy (e.g., power), and/or variance. In one embodiment, at least velocity and energy are estimated.

The ultrasound data represents a volume of a patient. The volume is scanned along different planes or other distribution of scan lines within the volume. The scanned volume is an interior of an object, such as the patient. Scanning the volume provides data representing the volume, such as representing a plurality of different planes in the object (e.g., patient). The data representing the volume is formed from spatial sampling of the object. The spatial samples are for locations distributed in an acoustic sampling grid in the volume. Where the acoustic sampling grid includes planar arrangements of samples, the spatial samples of the object include samples of multiple planes or slices.

Spatial samples along one or more scan lines are received. Where the transmit beam insonifies just one receive scan line, samples along that scan line are received. Where the transmit beam insonifies multiples scan lines, samples along the multiple scan lines are received. For example, receive beamforming is performed along at least thirty distinct receive lines in response to one broad transmit beam. To generate the samples for different receive beams, parallel receive beamformation is performed so that the different receive beams are sampled at a same time. For example, a system may be capable of forming tens or hundreds of receive beams in parallel. Alternatively, signals received from the elements are stored and sequentially processed.

Spatial samples are acquired for a plurality of receive lines in response to one transmit beam and/or in response to sequential transmit beams. Using broad beam transmission, spatial samples for multiple thin slices may be simultaneously formed using dynamic receive focusing (e.g., delay and/or phase adjust and sum). Alternatively, Fourier or other processing may be used to form the spatial samples.

The scanning may be performed a plurality of times. The acts are repeated to scan different portions of the region of interest. Alternatively, performing once acquires the data for the entire region of interest.

The complete region of interest is scanned at different times. Scanning at different times acquires spatial samples associated with flow. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Flow data is generated from the spatial samples. Any flow data, such as velocity, energy (power), and/or variance, may be generated. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. Color is used to distinguish from spectral Doppler imaging, where the power spectrum for a range gate is estimated. The change in frequency between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time. Multiple frames of flow data may be acquired to represent the region of interest at different times.

The estimation is performed for spatial locations in the volume. For example, velocities for the different planes are estimated from echoes responsive to the scanning.

The estimates may be thresholded. Thresholds are applied to the velocities. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

B-mode data is also acquired. One of the scans used for flow data estimation or a different scan is performed. The intensity of the echoes is detected for the different spatial locations.

For the volume, some spatial locations are represented by B-mode data and other locations are represented by flow data. Thresholding or other process is performed to avoid a location being represented by both B-mode and flow data. Alternatively, one or more locations may have values for both B-mode and flow data. While both types of data together represent the volume, the different types of data may be separately stored and/or processed or may be merged into one set representing the volume.

In act 32, flow data is filled. Due to thresholding or low echo returns, fluid regions may show little or no flow despite being adjacent to flow locations. The same locations may or may not have B-mode data. The flow holes are filled in act 32. The sensitivity may be increased as well.

Any approach for fill may be applied to the flow data of the volume. In one embodiment, multi-pass thresholding using spatial variance of velocity is used for color fill-in and sensitivity improvement. Acts 34-40 represent this approach. In general, different thresholds are applied, one to define a maximum extent of fill-in or flow region and the other to define a smaller, seed region for filling in the flow data.

In act 34, energy, velocity, and/or B-mode thresholds are applied at different levels in first and second passes to the B-mode and flow ultrasound data. The B-mode threshold is compared to the B-mode data to identify whether tissue exists. If tissue does not exist at the location, then the location may be associated with flow. Similarly, the energy and/or velocity thresholds are applied to corresponding flow data to determine whether the location is associated with flow. Higher energies and/or velocities indicate flow. Any now known or later developed color post-processing or thresholding may be used.

The first pass of thresholding is associated with lower flow thresholds than the second pass. The lower flow thresholds more likely identify locations as associated with flow. The lower flow thresholds provide higher sensitivity (fill-in), but higher noise and clutter. The second pass provides less sensitivity, but with lower noise and clutter. The flow from the second pass is used to identify locations within the flow region of the first pass, but with less noise and clutter than just using the flow locations from the first pass.

In act 36, a spatial variance of the velocity estimates is computed from the velocity data subjected to the first pass. Any size kernel may be used for determining variance, such as a 3×3×3 kernel. Velocity variance within the kernel is calculated.

In act 38, an adaptive threshold is determined. The threshold adapts to the energy estimates. For example, three-dimensional gradients are calculated from unfiltered energy estimates. Filtered energy estimates maybe used. Two or one-dimensional gradients may be used. The gradients are calculated throughout the volume associated with flow in the second pass, but flow in the first pass may be used. Any size kernel may be used for calculating the gradient, such as a 3×3×3 kernel.

The gradients indicate borders. Larger gradients are located at boundaries. For color fill-in, locations associated with a border are set to have a lower adaptive threshold. Any mapping of the gradient level to an adaptive threshold may be used, such as linear or non-linear maps. For example, gradients above one level of magnitude are associated with a low adaptive threshold and all other gradients are associated with a higher adaptive threshold. The adaptive threshold adapts as a function of the location. Providing a lower adaptive threshold may more likely expand or include the location at the flow boundary, growing the flow region to better reflect the actual fluid region despite the slower velocity and lesser energy of flow data at the border.

In act 40, the flow value for each location is set. The flow value is set as a function of three factors: the spatial variance, the energy (filtered or unfiltered), and the identification of flow from the second pass. For the spatial variance, locations associated with a spatial variance below a spatial variance threshold are identified. For the energy, locations associated with the energy estimate of the first pass being below the adaptive threshold are identified. For the second pass identification, locations associated with flow in the second pass are identified. In one embodiment, a one, two, or three-dimensional region is searched to determine locations associated with flow. For example, a 3×3×3 kernel is used. If a flow value in the second pass data indicates flow in an adjacent location or the location, then the location is indicated as associated with flow in the second pass.

If all three factors are true (e.g., spatial variance is small, energy above the adaptive threshold, and flow in the second pass data), then the flow data for the location is set to indicate flow. The flow data from the first pass for the location, flow data from the second pass for the location, or flow data from either pass for an adjacent location (e.g., average or same value) is used for the location.

Where one of the conditions is not met, then the flow data for that location is set to zero. For example, the velocity and energy values are set to zero.

Act 40 may be repeated or not repeated. Any number of repetitions may be used, such as two or three times. For each repetition, the flow data results of the previous iteration are used instead of the flow data from the second pass. The repetition may be fixed or adaptive, such as repeating until the flow region fails to grow or reaches a limit (e.g., a B-mode surface or boundary). This procedure increases the number of locations in the color region, improving the color fill-in and sensitivity.

Acts 32-40 are performed on data in the acoustic domain. The data is provided to a scan-converter and/or processor for conversion to a Cartesian coordinate system. Alternatively, acts 32-40 are performed on data interpolated to a Cartesian coordinate system, such as data on a regular 3D grid.

In an alternative embodiment, more than the thresholds vary between the first and second passes of act 34. For example, the settings for the clutter filter associated with estimation are changed. Dual-pass color estimation is performed. In the first estimation pass, a low pass clutter filter, a high-energy threshold and a low velocity threshold are used. The low pass clutter filter may remove flow information and maintain moving wall or tissue information. In the second estimation-pass, a conventional high pass clutter filter is applied to estimate based on flow. The energy threshold is used to limit the growing of the color region to the moving tissue region, and thereby suppress bleed.

In act 42, the boundaries or surfaces represented in the B-mode and/or flow data are enhanced for other processing. Act 42 may be performed prior to act 32 or 38 so that the borders may be more likely identified. Acts 44 and 46 enhance the edges represented in the B-mode and color data prior to rendering.

In act 44, gradients in the B-mode and flow data are determined. The gradient calculation is the same or different as used for act 38. For example, the same energy gradients are used in act 44, avoiding further calculation. Velocity and/or B-mode gradients are also calculated. In another embodiment, different gradient calculation is used. For example, gradients are calculated one-dimensionally in three orthogonal directions. A gradient vector is formed from the three gradients for each location. Any size kernel may be used, such as a 3×3×3 kernel.

In act 46, the B-mode and flow ultrasound data are filtered along surfaces. The surfaces are defined using the gradients. The surface is orthogonal to the gradient vector or direction. For each location, the B-mode and flow ultrasound data are filtered two-dimensionally or along a curved surface defined by the gradient direction. Any filtering may be used, such as low pass filtering. The low pass filtering smoothes the surface data, more likely making the surface distinct and/or continuous.

The identification of the B-mode and flow surfaces may be used for later processing. For example, the edge or boundary locations are provided for setting opacity as a function of ray depth.

Act 48 uses the enhanced B-mode and/or flow surfaces to determine an anatomy and anatomy orientation. Acts 50 and 52 provide one example, but other techniques for identifying anatomy may be used.

In act 50, one or more shapes are identified. The shapes are associated with the surfaces or borders. The B-mode, the flow, or both B-mode and flow shapes are identified.

Any shape identification algorithm may be used. For example, the surfaces are extracted by pattern matching, model fitting, border detection, or other process. In one embodiment, the B-mode and flow data with smoothed the edge locations output from act 46 are used. A morphological shape analysis (e.g., Hough transform) is performed on the B-mode and color surfaces to identify the respective shapes. The relative sizes, angles, general shapes (e.g., sphere verses ellipsoid) of different shapes are determined. A separate Radon transform may be used to determine the edge orientations.

In act 52, anatomy is identified by matching the identified shapes to a template. Any template matching may be used. In one embodiment, the correlation between a sequence of templates and the B-mode and flow data or gradients is determined. The template with the highest correlation identifies the shapes and/or the anatomy. In another embodiment, the separately identified shapes are matched to a template. For example, the relationship between the B-mode and color surfaces is examined. The local orientations and locations of the shapes are determined. If a flow boundary is contained within or closely matches a B-mode boundary, the anatomy is a chamber or a vessel wall. The characteristics of the shapes may be used to select a most similar template from a list of chamber or vessel templates. For example, the number of chambers, the number of color regions, the number of connected surfaces, the number of B-mode boundaries surrounding or adjacent to the color regions, and/or other characteristics (e.g., relative orientations) are determined from the shapes and used to index a collection of templates.

An anatomy template of a known view from prior studies or medical knowledge is selected based on the characteristics. The relationships between the B-mode and color surfaces may indicate specific views, such as apical 4-chamber, 2-chamber, long-axis, short-axis, sub-costal or another view. The closest match indicates the chosen view.

The view template may include other information. For example, anatomical landmarks are identified in the template. By selecting the template, anatomical landmarks from the template may be identified within the B-mode and/or flow volume. For example, the number, location, and names of valves and/or chambers are indicated. The anatomical landmark information may be added to a display or the data for rendering processed to highlight the landmarks.

In act 54, a viewing direction for rendering is received. The viewing direction is input by the user or automatically selected. The viewing direction indicates the direction, relative to the volume, from which the volume is to be viewed. The viewing direction may be from within the volume or outside of the volume. The viewing direction indicates the location of parallel or diverging rays for rendering the volume to a two-dimensional image.

In act 56, the viewing direction is used to determine values for one or more rendering parameters. The values are determined as a function of depth along the rays, the B-mode data, and the flow data. Along a given viewing direction, the values are determined from the B-mode and flow data. The B-mode data may be used for some ray depths, and flow data may be used for other ray depths. Thus, the values along the ray depth dimension are a function of both types of data.

Acts 58 and 60 are one example of performing act 56, but other approaches may be used. For example, opacity is determined as a function of the surfaces from act 46. The surfaces are determined from B-mode and flow data, so the values determined as a function of ray depth using the surfaces are determined as a function of B-mode and flow data. As another example, the values are determined as a function of location, regardless of the viewing direction. Different values are provided for different ray depths depending on the B-mode and/or flow data or quantities derived therefrom.

In act 58, gradients of the B-mode and flow ultrasound data are determined. The gradients from act 44 or 38 may be used, but other gradients may be calculated. In one embodiment, the gradients are determined in one dimension. The one dimension is along the viewing direction. The gradients along the view direction are calculated for the B-mode data and the flow data, providing B-mode gradients and flow gradients. The gradients are determined along each ray. The rays may correspond to display pixels or other distribution of ray lines.

In another alternative, data for a group of arrays is used. The largest gradient along each ray is used as the gradient for each of the arrays for the group or for a central ray. A moving window filters the gradients.

The gradients are determined in a first pass along ray lines. The rendering pipeline or a separate process may be used in multiple passes. Act 56 is performed in two passes, one for act 58 and another to perform act 60. Alternatively, acts 58 and 60 are performed in association with the first pass and rendering in act 72 is performed for the second pass.

The first pass determines gradients along the view direction. Since the volume is a combination of B-mode and flow data, the gradients from one pass may provide both B-mode and flow gradients. The gradient calculation for B-mode values does not use flow data, and the gradient calculation for flow data does not use B-mode data. At borders between the types of data, a gap in gradients may exist or a gradient value is extrapolated.

In act 60, the values for the at least one rendering parameter are determined. The values are determined as a function of ray depth in a second rendering pass along the ray lines.

Any rendering parameter may be used. For example, the opacity is determined as a function of ray depth. Values for opacity are set differently and/or independently for different depths along the ray lines. As another example, the decay or fade is determined as a function of ray depth.

In an opacity example, the values for the opacity are determined. A set of opacities are selected for the voxels along the ray. The values are based on the gradients. Different gradients or ranges of gradients are mapped to different opacities. Any mapping may be used, such as linear or non-linear mapping.

In one embodiment, the mapping is different for B-mode and flow data. B-mode opacity is set for different ray depths as a function of a B-mode gradient. Larger gradients may indicate a surface or border. For B-mode data representing tissue, the border tissue (e.g., heart or vessel wall) may be of particular importance in color flow imaging. The opacity is set such that larger gradients correspond to larger opacity. The opacity values are set to be more opaque for locations with greater B-mode gradients and to be less opaque for locations with lesser B-mode gradients. Increasing the opacity for large B-mode gradients may better highlight the edge or walls. For small B-mode gradients, the B-mode opacity is decreased to improve the visualization of the wall and flow. For decay, the decay is increased for small gradients and vice-versa.

For flow data, flow opacity is set for ray depths as a function of the flow gradient of the flow ultrasound data. The opacity is set such that larger flow gradients correspond to smaller opacity. The values of the opacity for ray depths associated with flow data are more opaque for locations with lesser flow gradient and less opaque for locations with greater flow gradient. This opacity mapping emphasizes the interior or regions of greater flow. The locations of large flow gradients along the ray may be associated with flow edges. The opacity at the flow edge closest to the ray is reduced, and the opacity towards the center is increased to provide a translucent (e.g., see-through) appearance for flow. For decay, the decay is decreased for small gradients and vice versa.

In an alternative embodiment, the centroid of the flow region is computed. For example, a one-dimensional centroid is determined along each ray. The flow opacity in both directions away from the centroid is reduced.

In act 62, bleed and/or noise in the flow data is reduced prior to rendering. Noise and bleed tend to be reflected in velocity information, so act 62 is applied to velocity data. Act 62 may be applied for other flow data, such as energy data. Any bleed or noise reduction may be used, such as spatial filtering or thresholding. Acts 64-68 are one example for bleed and noise reduction. Multi-pass thresholding is performed using velocity, unfiltered energy, and B-mode data.

In act 64, in a first pass along the rays, the velocity and energy data are compared to noise and bleed thresholds. The energy estimates are compared to an energy noise threshold and an energy bleed threshold, and the velocity estimates are compared to a velocity noise threshold and a velocity bleed threshold. If along the ray, the energy, $U \leq U\_noise$ and $abs(V) > Vel\_noise$, then the flow at that location is a noise pixel. If along the ray, $U > U\_bleed$ and $abs(V) \leq Vel\_bleed$, then the flow at that location is bleed. Other thresholds or relationships may be used.

In act 66, the flow data, rendering parameter, or both is set to remove the noise or bleed information. For example, the velocity estimates or the opacity are set to zero for locations where the energy estimate is below the energy noise threshold and the velocity estimate is above the velocity noise threshold. The same is done for locations where the energy estimate is above the energy bleed threshold and the velocity estimate is below the velocity bleed threshold. Any threshold levels may be used. The thresholds for noise or bleed may be fixed, selectable, or adaptive. In one embodiment, the thresholds depend on a selected imaging application. Thresholds appropriate for other imaging settings in the application are selected.

In act 68, the values of the rendering parameter are altered for the B-mode data between locations along the viewing direction with flow data above a gradient threshold. After setting the values in act 60, the values may be further altered. Alternatively, the setting of values in act 60 accounts for location of B-mode surfaces relative to flow surfaces. The B-mode edges or borders are compared with the flow edges or borders along the ray lines. If a B-mode surface lies between two flow surfaces, the opacity of flow data for the region or ray depths between the B-mode surface and the flow surface closest to the viewer is reduced to suppress bleed.

In act 70, the contribution of B-mode data may be limited. The B-mode data or opacity is set to zero for B-mode data with a gradient below a threshold. The gradient is from the gradient of act 58, 44, or 38. Alternatively, a separate gradient is determined. Gradients below a threshold indicate interior tissue regions. For imaging flow, such regions may have less significance. By setting to zero, the flow is imaged with only specific B-mode targets being included in the image. For example, chamber walls are associated with greater gradients, so are shown, and surrounding tissue is not shown or shown with high transparency.

The opacities used for B-mode data may be different than or set relative to the opacities used for flow data. For example, B-mode data is made more transparent to better highlight the flow information.

In act 72, an image is rendered from the B-mode and flow ultrasound data. The rendering is a function of the viewing direction and the values for the at least one rendering parameter. For example, the image is rendered as a function of the values for the opacity, the B-mode data, and the flow data. During rendering, the B-mode opacity values are applied to B-mode data, and the flow opacity values are applied to the flow data. The opacity values weight the relative contribution of the data along each ray line. Data with greater opacity is more heavily weighted, resulting in greater relative contribution to the displayed pixel.

Any rendering may be used, such as maximum, minimum, or mean projection along view lines. Data from the nearest two, three, or four locations are interpolated to each sample point along each view line. The data along the view line is used for rendering.

Shading may be used. One or more light sources may be used for shading. The light source position or number may be based on the identified surfaces and edges. For example, a light source is placed near the virtual viewer location and at the center of a heart chamber to highlight the walls.

Figure 2A:
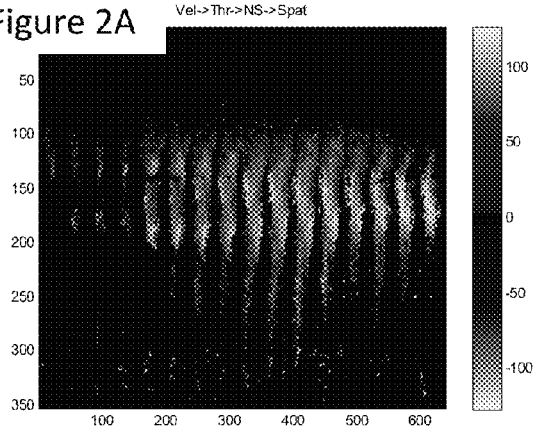
FIGS. 2A and 3A are example 3D rendered images generated using conventional processes.
Figure 2B:
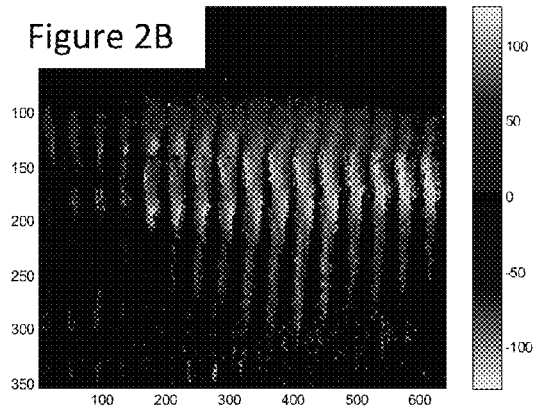
FIGS. 2B and 3B are example 3D rendered images generated using adaptive processing, in accordance with a specific embodiment of the invention.

FIGS. 2A-2B and 3A-3B represent volume rendering using alpha blending along ray lines. Different acts are highlighted for the different Figures. FIGS. 2A and 2B show rendering without using act 32 and with using the fill-in of act 32, respectively. The other data or rendering altering acts, such as the rendering parameter value determination of act 56, are not performed in FIG. 2. In FIG. 2B, the kernel size is 3×3×3. The number of repetitions was 1.

Figure 3A:
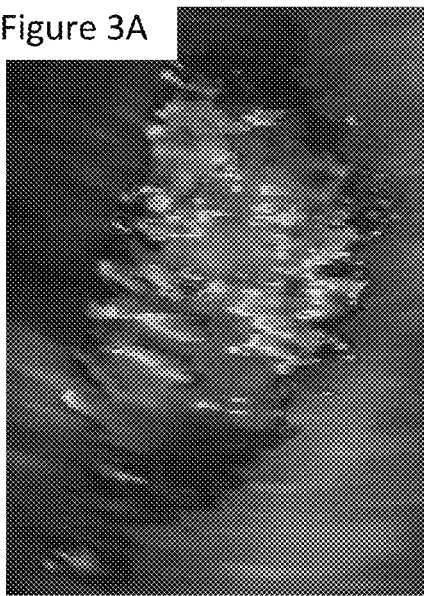
Figure 3B:
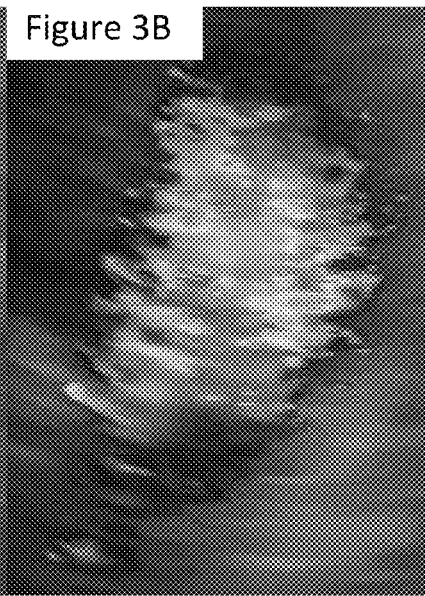

FIGS. 3A and 3B show rendering without performing act 56 and with performing act 56, respectively. The other data or rendering altering acts, such as the fill-in of act 32, are not performed. For FIG. 3B, a one-dimensional gradient along the rays is used. The opacity map for flow is based on depth, velocity and energy. The centroid computation option was not used. Only one light source at the viewer was used.

The anatomy information determined in act 48 may have other uses. The rendered image may be enhanced based on the anatomy. For example, the B-mode regions are textured prior to rendering to better distinguish between types of tissue. The texturing may reduce speckle by spatial filtering. Contrast at surfaces may be enhanced by high pass filtering orthogonal to a surface and low pass filtering along the surface. Using the template information, clinical markers, such as wall boundaries and valves, may be highlighted by increasing opacity and/or filtering.

Automatic imaging adjustment may be provided. The gain and dynamic range of the data may be altered. For example, fluids have little attenuation. The gain and dynamic range applied to the data may be adjusted to account for variations in attenuation based on fluid regions. Depth-gain curves are selected as a function of the fluid region locations relative to the transducer.

The frequency or other imaging parameter used in subsequent scans may be adjusted based on the type of anatomy. For example, an imaging application or preset is selected based on the determined anatomy. If the heart is being imaged, then a preset to better show jets may be used.

The flow region of interest may be further enhanced. Fill-in may account for B-mode surfaces. The B-mode surface is used to limit the fill-in region.

Aliasing may be reduced and the flow angle corrected based on expected anatomical flow. For example, the expected flow is determined from the boundary conditions obtained from the B-mode data and the flow dynamics based on prior frames. The expected flow is compared with the current flow to correct the flow aliasing and improve the fill-in. The B-mode surface in the heart changes over time. The angle of the scan lines to the motion may result in inaccurate motion information. By angle correcting the flow data based on the expected flow or motion direction, greater fill-in may be provided due to larger boundary flow data.

The anatomy may be used for automatically selecting an automated calculation package. Different calculations are appropriate for different anatomy. For imaging the heart, automatic volume quantification for color may be used. Similarly, automatic computations of statistics are provided for left ventricle analysis, right ventricle analysis, regurgent flow analysis, or other anatomy appropriate analysis.

Relative terminology, such as associated with threshold settings, indicates a difference between values. For example, lower and higher thresholds are thresholds with relative difference, rather than absolutes. Different imaging situations may have different values, based on experimentation, dynamic range, imaging system, and/or user preference. The actual values may be any value.

Figure 4:
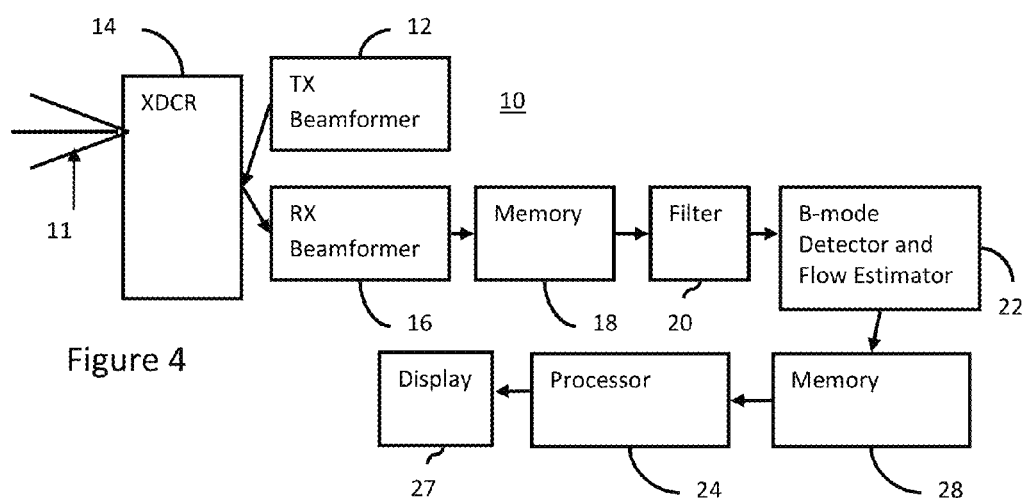
FIG. 4 is a block diagram of one embodiment of a system for adaptive volume rendering.

FIG. 4 shows one embodiment of a system 10 for adaptive three-dimensional flow imaging in medical diagnostic ultrasound. The system 10 includes a transmit beamformer 12, a transducer 14, a receive beamformer 16, a memory 18, a filter 20, a B-mode detector and flow estimator 22, a memory 28, a processor 24, and a display 27. Additional, different or fewer components may be provided. For example, the system includes the B-mode detector and flow estimator 22 and processor 24 without the front-end components such as the transmit and receive beamformers 12, 16. In one embodiment, the system 10 is a medical diagnostic ultrasound system. In an alternative embodiment, the system 10 is a computer or workstation. In yet another embodiment, the B-mode detector and flow estimator 22 is part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. In one embodiment, the transmit beamformer 12 transmits beams sufficiently large to cover at least thirty distinct receive lines, and the receive beamformer 16 receives along these distinct receive lines in response to the transmit beam. Use of the broad beam transmit and parallel receive beamforming along tens or hundreds of receive lines allows for real-time scanning of multiple slices or a volume. The receive lines and/or transmit beams are distributed in the volume, such as the receive lines for one transmit being in at least two different planes. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pursers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 30, 40, or 50) receive beams in response to each transmit beam. The receive beams are collinear, parallel and offset or non-parallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 identifies velocity information from slower moving tissue as opposed to fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The B-mode detector and flow estimator 22 is a Doppler processor or cross-correlation processor for estimating the flow data and a B-mode detector for determining the intensity. In alternative embodiments, another device now known or later developed for estimating velocity, energy, and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The energy and variance may also be calculated.

Flow data (e.g., velocity, energy, or variance) is estimated for spatial locations in the scan volume from the beamformed scan samples. For example, the flow data represents a plurality of different planes in the volume.

The flow estimator 22 may apply one or more thresholds to identify sufficient motion information. For example, velocity and/or energy thresholding for identifying velocities is used. In alternative embodiments, a separate processor or filter applies thresholds. The B-mode detector and flow estimator 22 outputs B-mode and flow data for the volume.

The memory 28 is video random access memory, random access memory, removable media (e.g. diskette or compact disc), hard drive, database, or other memory device for storing B-mode and flow data. The stored data is in a polar or Cartesian coordinate format. The memory 28 is used by the processor 24 for the various filtering, rendering passes, calculations or other acts described for FIG. 1. The processor 24 may additionally reformat the data, such as interpolating the data representing the volume to a regularly spaced Cartesian coordinate 3D grid.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 18, 28, or a different memory for adaptive volume rendering in medical diagnostic ultrasound.

The processor 24 receives B-mode and flow data from the B-mode detector and flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 causes generation of an image as a two-dimensional image representing a volume from a viewing direction. The image is rendered from B-mode and flow data. The rendering is performed using rendering parameters. One or more of the rendering parameters may have adaptive values. For example, the values are different for different locations. Along a ray line for rendering, the opacity and/or fade may have different values depending on the B-mode and flow data along the ray line.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

In one embodiment, the instructions are for performing rendering. The rendered voxel color and opacity is a function of ultrasound parameters. For example, the color=f(B-mode/velocity/energy/variance, viewing-depth, gradient magnitude, . . . ), where f(.) is some RGB transfer function, and opacity=g(B-mode/velocity/energy/variance, viewing-depth, gradient magnitude, . . . ), where g(.) is some opacity transfer function. Ray tracing is done using these two voxel values.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed:

1. A method for adaptive volume rendering in medical diagnostic ultrasound, the method comprising:
   acquiring B-mode and flow ultrasound data representing a volume of a patient, wherein the flow ultrasound data includes energy and velocity estimates;
   applying energy and velocity thresholds at different levels in first and second thresholding passes to the same flow ultrasound data, the first thresholding pass associated with lower thresholds than the second thresholding pass;
   computing a spatial variance of the velocity estimates subjected to the first thresholding pass;
   determining an adaptive threshold as a function of three-dimensional gradients calculated from the energy estimates subjected to the second thresholding pass, wherein the adaptive threshold is lower for larger gradients and higher for lower gradients; and
   for each location associated with flow ultrasound data subjected to the first thresholding pass, identifying locations with the spatial variance below a spatial variance threshold and the energy estimate below the adaptive threshold, identifying that the flow data subjected to the second thresholding pass indicates flow within a neighborhood of locations around the location, and setting the flow data to show flow, otherwise showing no flow;
   receiving a viewing direction relative to the volume;
   determining values for at least one rendering parameter as a function of depth along the viewing direction, the B-mode ultrasound data, and the flow ultrasound data; and
   rendering an image from the B-mode and flow ultrasound data, the rendering being as a function of the viewing direction and the values for the at least one rendering parameter.

2. The method of claim 1 wherein determining comprises determining B-mode gradients along the viewing direction from the B-mode ultrasound data and determining flow gradients along the viewing direction from the flow ultrasound data.

3. The method of claim 1 wherein determining comprises determining gradients of the B-mode and flow ultrasound data in a first rendering pass, and determining the values for the at least one rendering parameter as a function of depth in a second rendering pass.

4. The method of claim 1 wherein determining comprises determining the values for opacity as a function of the depth along the viewing direction.

5. The method of claim 4 wherein determining the opacity comprises setting a B-mode opacity for depths along the viewing direction as a function of a B-mode gradient of the B-mode ultrasound data such that larger gradients correspond to larger opacity and setting a flow opacity for depths along the viewing direction as a function of a flow gradient of the flow ultrasound data such that larger gradients correspond to smaller opacity, the B-mode opacity applied to B-mode data during the rendering and the flow opacity applied to the flow data during the rendering.

6. The method of claim 1 wherein determining comprises determining the decay or fade as a function of the depth along the viewing direction.

7. The method of claim 1 wherein determining comprises determining the decay or fade as a function of the depth along the viewing direction, b-mode intensity, color velocity or color energy.

8. The method of claim 1 further comprising:
   comparing the energy estimates to an energy noise threshold and an energy bleed threshold data and comparing the velocity estimates to a velocity noise threshold and a velocity bleed threshold;
   setting the velocity estimates or the rendering parameter to zero for locations where the energy estimate is below the energy noise threshold and the velocity estimate is above the velocity noise threshold and for locations where the energy estimate is above the energy bleed threshold and the velocity estimate is below the velocity bleed threshold; and
   altering the values of the at least one rendering for the B-mode data between locations along the viewing direction with flow data above a gradient threshold.

9. The method of claim 1 further comprising setting the B-mode data to zero or the rendering parameter to zero for B-mode data with gradient below a threshold.

10. The method of claim 1 further comprising:
    determining gradients in the B-mode and flow ultrasound data; and
    low pass filtering the B-mode and flow ultrasound data along surfaces defined as a function of the gradients.

11. The method of claim 10 further comprising:
    identifying shapes associated with the surfaces; and
    selecting a template as a function of the shapes, the template indicating anatomical landmarks.

12. In a non-transitory computer readable storage medium having stored therein data representing instructions executable by a programmed processor for adaptive volume rendering in medical diagnostic ultrasound, the storage medium comprising instructions for:
    receiving B-mode data and flow data representing a volume, locations in the volume corresponding to either B-mode data or flow data, wherein the flow ultrasound data includes energy and velocity estimates;
    determining B-mode gradients along ray lines;
    determining flow gradients along the ray lines;
    applying energy and velocity thresholds at different levels in first and second thresholding passes to the same flow ultrasound data, the first thresholding pass associated with lower thresholds than the second thresholding pass;
    computing a spatial variance of the velocity estimates subjected to the first thresholding pass;
    determining an adaptive threshold as a function of three-dimensional gradients calculated from the energy estimates subjected to the second thresholding pass, wherein the adaptive threshold is lower for larger gradients and higher for lower gradients; and
    for each location associated with flow ultrasound data subjected to the first thresholding pass, identifying locations with the spatial variance below a spatial variance threshold and the energy estimate below the adaptive threshold, identifying that the flow data subjected to the second thresholding pass indicates flow within a neighborhood of locations around the location, and setting the flow data to show flow, otherwise showing no flow;
    setting values for opacity as a function of depth along the ray lines, the values of the opacity for depths associated with flow data being more opaque for locations with lesser flow gradient and being less opaque for locations with greater flow gradient, and the opacity for depths associated with B-mode data being more opaque for locations with greater B-mode gradients and being less opaque for locations with lesser B-mode gradients; and rendering an image as a function of the values for the opacity, the B-mode data, and the flow data.

13. The non-transitory computer readable medium of claim 12 wherein determining comprises determining B-mode and flow gradients in a first rendering pass along the ray lines, and determining the values as a function of ray depth in a second rendering pass along the ray lines.

14. The non-transitory computer readable medium of claim 12 further comprising:
comparing the energy estimates to an energy noise threshold and an energy bleed threshold data and comparing the velocity estimates to a velocity noise threshold and a velocity bleed threshold;
setting the velocity estimates or the rendering parameter to zero for locations where the energy estimate is below the energy noise threshold and the velocity estimate is above the velocity noise threshold and for locations where the energy estimate is above the energy bleed threshold and the velocity estimate is below the velocity bleed threshold; and
altering the values for the B-mode data between locations along the ray lines with flow data above a gradient threshold.

15. The non-transitory computer readable medium of claim 12 further comprising setting the B-mode data to zero or the rendering parameter to zero for B-mode data with the B-mode gradient below a threshold.

16. The non-transitory computer readable medium of claim 12 further comprising low pass filtering the B-mode and flow data along surfaces defined as a function of the B-mode and flow gradients, respectively.

17. The non-transitory computer readable medium of claim 16 further comprising:
identifying shapes associated with the surfaces; and
selecting a template as a function of the shapes, the template indicating anatomical landmarks.

* * * * *